United States Patent [19]

Bier

[11] 4,040,940
[45] Aug. 9, 1977

[54] ELECTROPHORETIC FRACTIONAL ELUTION APPARATUS EMPLOYING A ROTATIONAL SEAL FRACTION COLLECTOR

[75] Inventor: Milan Bier, Tucson, Ariz.

[73] Assignee: The United States of America as represented by the Secretary of the Department of Health, Education and Welfare, Washington, D.C.

[21] Appl. No.: 753,103

[22] Filed: Dec. 21, 1976

[51] Int. Cl.² ............... G01N 27/26; G01N 27/28
[52] U.S. Cl. ......................... 204/299 R; 204/180 G
[58] Field of Search .......... 204/180 S, 180 R, 180 G, 204/299, 300, 304; 233/11

[56] References Cited

U.S. PATENT DOCUMENTS

| | | | |
|---|---|---|---|
| 2,849,394 | 8/1958 | Waterman | 204/304 |
| 2,992,979 | 7/1961 | Magnuson et al. | 204/180 S |
| 3,197,394 | 7/1965 | McEuen | 204/300 X |
| 3,238,115 | 3/1966 | Pedersen | 204/300 |
| 3,303,120 | 2/1967 | Hrdina | 204/300 |
| 3,844,926 | 10/1974 | Smyth et al. | 204/299 |
| 3,927,826 | 3/1976 | Anderson et al. | 233/11 |
| 4,008,135 | 2/1977 | Gazda | 204/300 X |

*Primary Examiner*—Arthur C. Prescott
*Attorney, Agent, or Firm*—Browdy and Neimark

[57] ABSTRACT

Electrophoretic fractional elution apparatus has a column with a rotating seal joint at which a thin jet of eluting buffer is directed across the lumen of the electrophoretic column in a direction perpendicular to that of electrophoretic migration. Either the content of the column is rotated with respect to the stationary jet, or the jet is rotated with respect to the column. The system may employ electrophoresis either in free solution or in packed columns.

12 Claims, 13 Drawing Figures

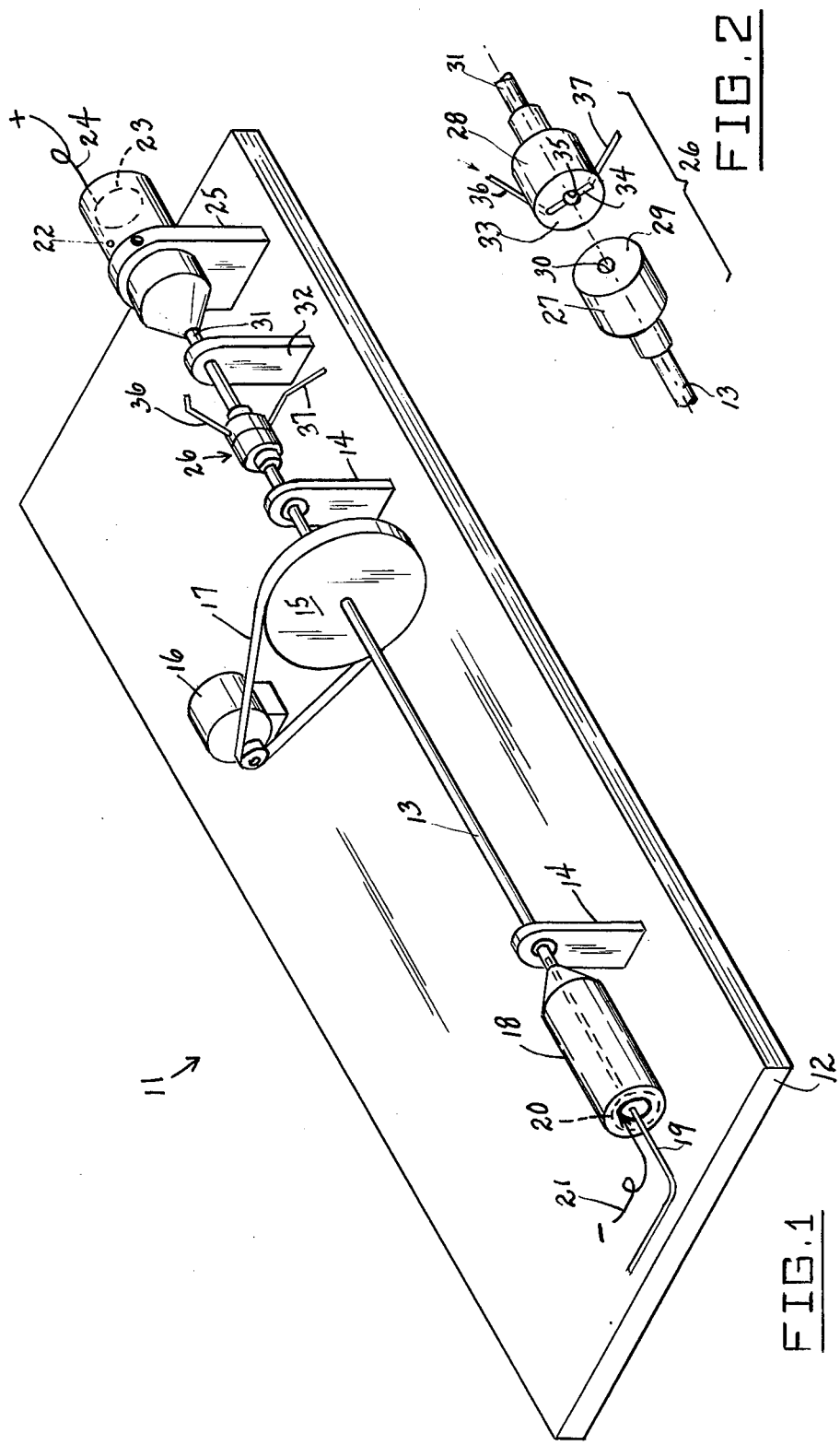

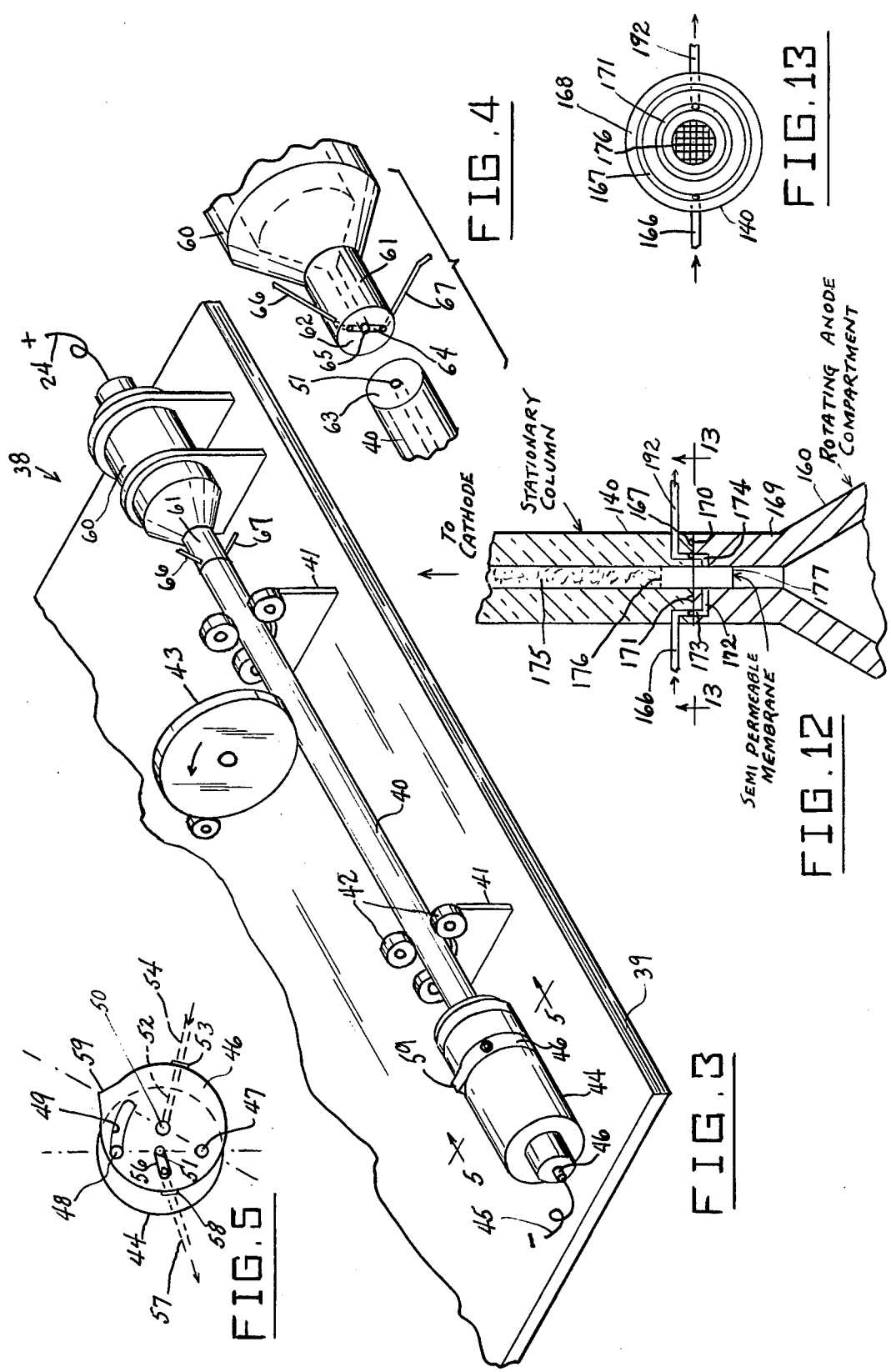

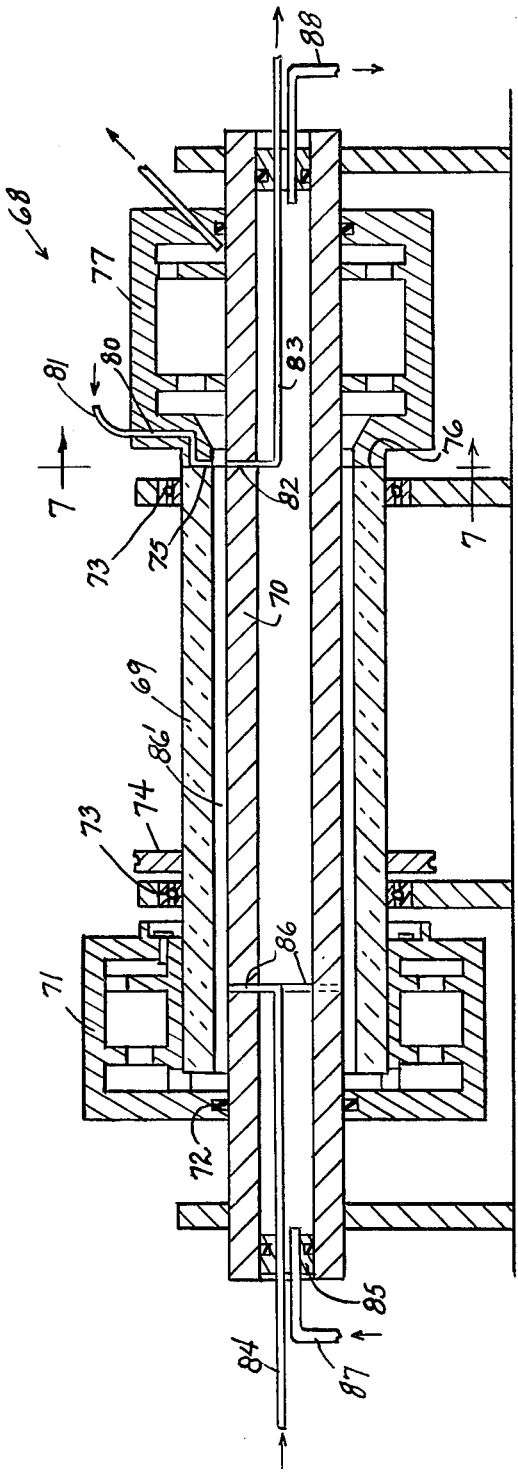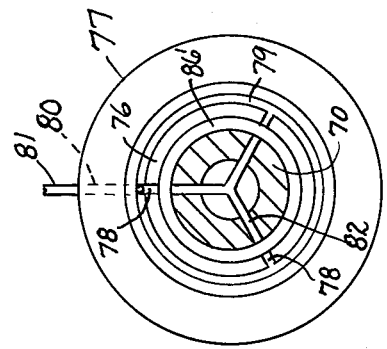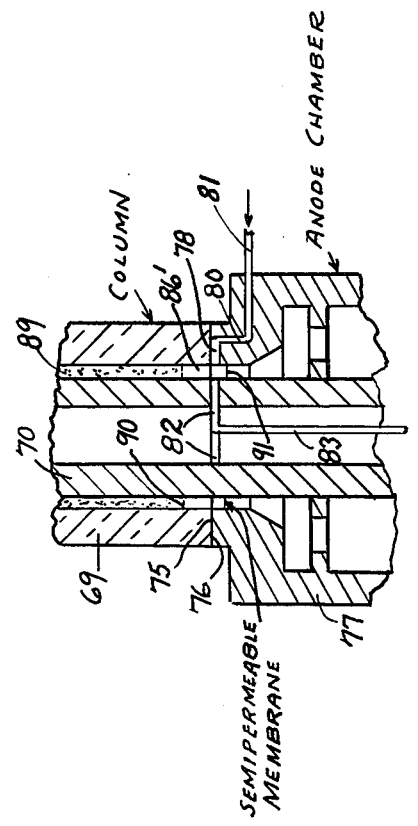

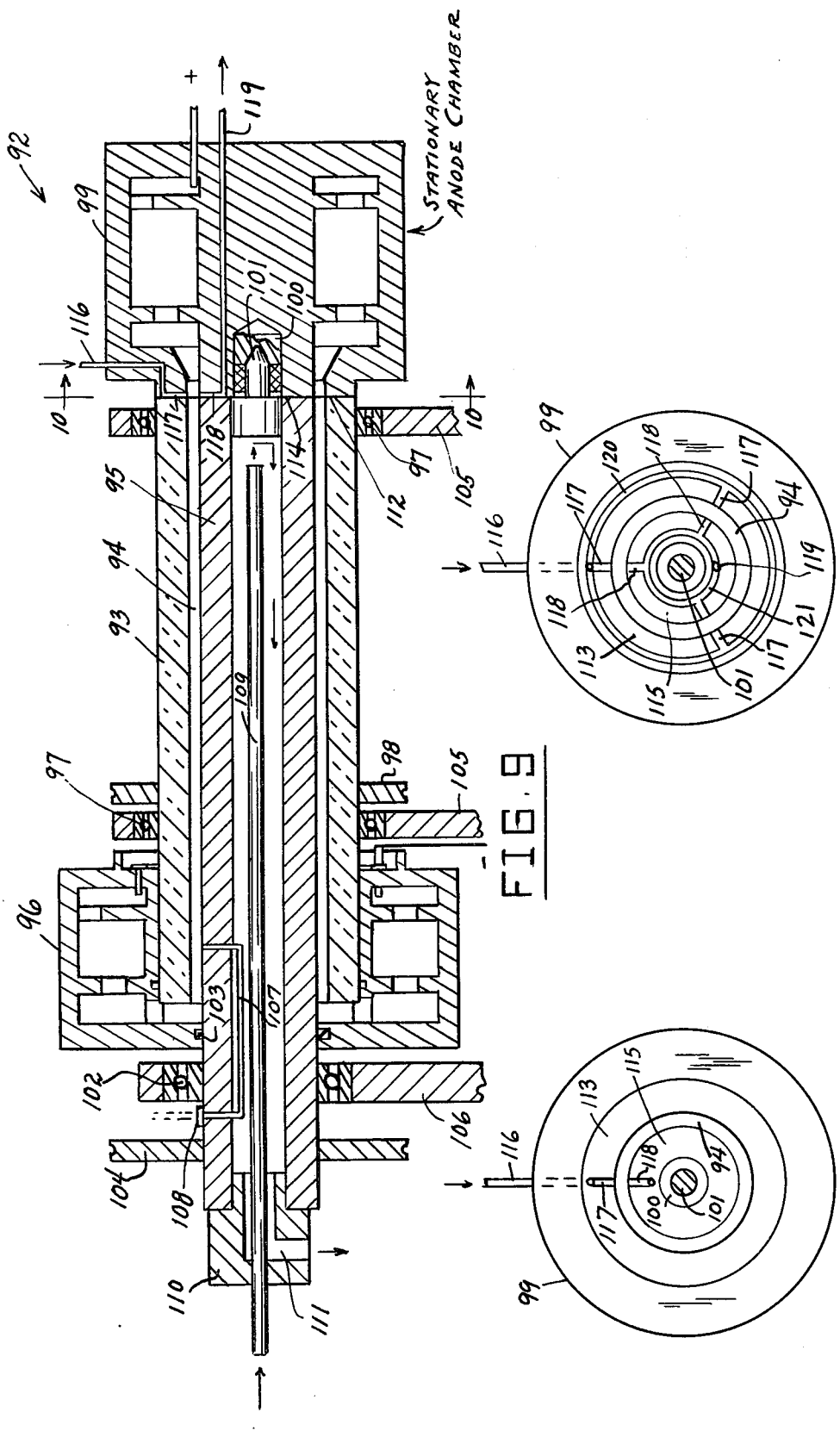

ELECTROPHORETIC FRACTIONAL ELUTION APPARATUS EMPLOYING A ROTATIONAL SEAL FRACTION COLLECTOR

FIELD OF THE INVENTION

This invention relates to apparatus for the electrophoretic separation of soluble or particulate ionized matter, and more particularly to an electrophoresis apparatus employing an elution jet directed perpendicularly to the direction of electrophoretic migration.

BACKGROUND OF THE INVENTION

The electrophoretic process of separation of soluble or particulate ionized matter is potentially complicated by convective effects. These may be caused by unequal temperature distribution, due to Joule heating, or unequal solute concentration, due to resolution of the sample into sharply compartmentalized individual zones. Stabilization against these convective disturbances is essential. The most common way to avoid convection is to work in gels, or columns packed with finely dispersed matter, such as glass beads, agarose granules, starch granules, etc., whereby electrophoresis is carried out in the interstitial capillary bed formed by these materials. Another way to stabilize against convective flow is to create a density gradient using an inert solute, such as sucrose. A third way was developed by Hjerten[*], who utilized horizontal tubes, slowly rotating around their axis. Thus, gross convection is avoided, because of the continuous change in the direction of the gravity vector. This is akin to the commonly used clinostats in biological experiments.

[*] S. Hjerten: "Free Zone Electrophoresis", Almqvist & Wiksells, Uppsala, 1967.

No matter what principle of stabilization is employed, separation is easily achieved by the application of a D.C. electrical field. The major problem is not to achieve separation, but the actual physical isolation of the separated fractions. A number of techniques have been used, as for example, simple sectioning of gels, elution of powder-filled columns, separation of samples by means of careful aspiration with a syringe, interposition of a sample-impermeable dialyzing membrane in the migration pathway coupled with a transverse flow of buffer over the surface of the membrane, draining of density stabilized columns, etc.

A preliminary search of the prior art revealed the following U.S. Pat. Nos. as representing what appeared to be the best prior art relating to the subject matter of the present invention: Anderson et al., 3,927,826, Waterman, 2,849,394, Magnusen et al., 2,992,979, Smyth et al. 3,844,926.

The U.S. Pat. No. to Smyth et al. 3,844,926 shows a separating apparatus suitable for electrophoretic separation and including an uninterrupted annular chamber defined by coaxial outer and inner walls, wherein the outer wall rotates. The electric field is radially oriented across the lumen.

Magnusen et al. 2,992,979 show a combination of centrifugal field and an electrical field to enhance electrophoretic separation. The electrophoresis is practiced on a sheet of absorbent material to stabilize the fluid system.

The Anderson et al. U.S. Pat. No. 3,927,826 shows the formation of electrophoresis gels using a rotor. Waterman 2,849,394 uses a rotating system including a rotating electrode for coalescing.

Thus, the need exists for a simple means of withdrawing fractions from an axially oriented electrophoresis tube particularly in the field of cell electrophoresis, such as for the separation of living cells, e.g. blood cells.

SUMMARY OF THE INVENTION

The present invention deals with a novel way of fraction collection. It is addressed primarily to electrophoretic devices of concentric tubular design: either simple tubes, or instruments where separation is carried out in the lumen between two concentric glass tubes. The latter design is used to increase the surface-to-volume ratio for better cooling. The essence of the present invention is the use of a rotating seal fraction collector wherein a thin jet of eluting buffer is directed across the lumen of the electrophoretic device, in a direction perpendicular to that of electrophoretic migration, this fluid jet sweeping with it all the migrating particles in its pathway. Complete elution of the lumen is achieved by rotating the jet with respect to the lumen, or rotating the lumen with respect to the eluting jet.

This principle of sample elution by means of a rotating seal fraction collector permits the design of a variety of electrophoretic devices. Thus, the rotating seal fraction collector can be used either with gel or granule-packed columns, or also in free solutions, utilizing the principle of rotationally-stabilized fluids, according to the original discovery of Hjerten. The main advantage of this latter arrangement is that the apparatus becomes applicable also to separation of particulate matter, such as living cells, such as blood cells, bacteria, etc., which cannot be separated in packed columns because of their large size.

Accordingly, an object of the invention is to provide a novel and improved means for elution of separated fractions from rotationally stabilized electrophoresis tubes containing free fluid, or in packed columns, said means employing a rotating seal fraction collector.

A further and more general object is to overcome the deficiencies of the prior art, such as those mentioned above.

Another object is to provide for improved elution of fractions separated by electrophoresis.

A further object of the invention is to provide improved means for elution of separated fractions from rotationally stabilized electrophoresis channels formed by the lumen between two concentric cylinders, containing free fluid, said means comprising a rotating seal fraction collector.

A still further object of the invention is to provide improved means for elution of separated fractions from electrophoretic columns packed with gels, powders, or other anti-convective materials, said means comprising a rotating seal fraction collector.

A still further object of the invention is to provide improved electrophoresis instruments comprising means for sample injections, rotational stabilization of fluid contained within either the lumen of a single tube or the lumen between two concentric cylinders, and a rotating seal fraction collector for the elution of separated fractions, adapted to be readily employed with means for refrigerating said instruments.

A still further object of the invention is to provide improved electrophoresis instruments comprising means for sample injection, stabilization of fluid by means of gels or granular anti-convective packing materials within the bore of a single tube or the lumen between two concentric cylinders, and a rotating seal fraction collector for the elution of separated fractions, readily usable with means for refrigerating said instruments.

BRIEF DESCRIPTION OF THE DRAWINGS

Further objects and advantages of the invention will become apparent from the following description of embodiments, and from the accompanying drawings thereof, wherein:

FIG. 1 is a perspective view of an electrophoresis apparatus according to the present invention, using a rotationally stabilized electrophoresis tube with a rotating seal fraction collector.

FIG. 2 is an enlarged perspective view of the components of the rotating seal fraction collector employed in FIG. 1, shown in separated and mutually angled positions.

FIG. 3 is a perspective view of another electrophoresis apparatus according to the present invention, also using a rotationally stabilized electrophoresis tube.

FIG. 4 is an enlarged perspective view showing the components of the rotating seal fraction collector of the apparatus of FIG. 3, the components being shown in separated, mutually angled positions.

FIG. 5 is an enlarged transverse vertical cross-sectional view taken substantially on the line 5—5 of FIG. 3, but showing the pivotally sliding sample-injection gate in sample-filling position.

FIG. 6 is a longitudinal vertical cross-sectional view taken through another form of electrophoresis apparatus according to the present invention, using concentric cylinders defining a lumen therebetween.

FIG. 7 is a transverse vertical cross-sectional view taken substantially on line 7—7 of FIG. 6.

FIG. 8 is a fragmentary vertical cross-sectional view taken through the rotating seal portion of a vertically-positioned electrophoresis apparatus similar to that of FIG. 6, employing packed anti-convection material in the lumen defined between the concentric cylinders.

FIG. 9 is a longitudinal vertical cross-sectional view of another form of electrophoresis apparatus according to the present invention, using concentric cylinders defining a lumen therebetween, wherein both cylinders are rotatable.

FIG. 10 is a transverse vertical cross-sectional view taken substantially on line 10—10 of FIG. 9.

FIG. 11 is a transverse vertical cross-sectional view similar to FIG. 10, but showing a modification.

FIG. 12 is a fragmentary vertical cross-sectional view taken through the rotating seal portion of a vertically-positioned electrophoresis apparatus generally similar to that of FIG. 3, but modified as to relative rotation of the parts and employing packed anti-convective material in the stationary column thereof.

FIG. 13 is an enlarged horizontal cross-sectional view taken substantially on line 13—13 of FIG. 12.

DESCRIPTION OF PREFERRED EMBODIMENTS

Referring to the drawings, FIG. 1 illustrates a relatively simple embodiment of a rotationally stabilized electrophoresis tube assembly provided with a rotating seal fraction collector in accordance with the present invention, the assembly being designated generally at 11. The assembly 11 comprises a supporting base plate 12 on which a rotating glass or plastic tube 13 is supported on bearing blocks 14, 14. Tube 13 is provided with a pulley 15 which is driven by a motor 16 by means of a belt 17. A cathode electrode compartment 18 is sealingly and rigidly coaxially secured to one end of tube 13 and rotates with the tube. A capillary tube 19 extends axially, rotatably, and sealingly through the end wall of compartment 18 and is suitably supported so that its inner end protrudes into the bore of the rotating glass or plastic tube 13 without substantially obstructing its lumen. The cathode electrode, shown diagrammatically at 20, is energized from a negative voltage supply line 21 by a suitable conventional brush and slip ring assembly. Electrode 20 may be a non-gasing silver electrode, or other similar reversible electrode.

At the other end of the assembly, in axial alignment with tube 13, is the anode compartment 22, provided with the anode 23 which is connected to the positive voltage supply wire 24. Anode compartment 22 is mounted in an upstanding bracket 25 and is adjustably secured therein in a non-rotative condition. The rotating seal fraction collector assembly is designated generally at 26 and comprises two mating generally cylindrical adaptor blocks 27 and 28 machined from suitable material, such as Teflon, nylon, glass, or other suitable material. Block 27 is coaxially mounted on the end of tube 13 and has a flat end surface 29 perpendicular to its rotational axis, its bore or lumen 30 being in communication with the bore or lumen of the rotating tube 13. Similarly, block 28 is communicatively connected rigidly to the stationary tube segment 31, supported on an upstanding bracket or block 32, in turn rigidly communicatively connected to anode compartment 22. Adaptor block 28 is symmetrically similar to block 27 and has a flat end surface 33 perpendicular to its axis and sealingly engaged by the rotating end surface 29 of block 27. Surface 33 is formed with a diametrically oriented narrow groove or channel 34 traversing the lumen or bore 35 of block 28.

The narrow channel 34 directs the eluting fluid jet perpendicularly across the axis of rotation of tube 13, and block 28 is provided with an afferent elution fluid feed tube 36 connected to a passage leading to one end of groove or channel 34 and with an efferent fluid outlet tube 37 connected to a passage leading to the other end of groove or channel 34. Thus, adaptor block 27 rotates, since it is axially fixed to tube 13, while adaptor block 28 is stationary, since it is axially fixed to tube 31 and stationary anode compartment 22.

In the arrangement of FIG. 1 the eluting fluid jet traversing the lumen 35 is stationary and the fluid contents of the electrophoresis column or tube assembly is rotating, though at a somewhat slower rate than the tube 13, due to interaction of the rotating fluid contents with the relatively stationary fluid near the anode compartment.

To operate the apparatus 11, first all compartments are filled with an appropriate buffer and all air is excluded. Filling is accomplished by means of suitable feed ports in the electrode compartments, which can be subsequently sealed. Compartment 22 is adjusted to provide sealing cooperation of the mating surfaces 29, 33. The flow of the eluting buffer is started and maintained, using a constant feed infusion pump, such as a syringe pump, not shown, connected to the afferent tube 36. The two mating surfaces 29, 33 of the rotating seal fraction collector assembly 26 must be wetted by the eluting buffer, or otherwise lubricated, to prevent an air bubble from entering into the electrophoresis channel. For this purpose regulation of hydrostatic pressure in the efferent tube 11 may be necessary, its free end being held at a level preferably somewhat lower than the axis of rotation of the assembly 26.

The composition of this eluting buffer should be the same as the buffer originally filling the electrophoresis tube and anode compartment. Its continuous flow will therefore not alter the composition of the medium in which electrophoresis is carried out. The sample is injected into the tube 13, via capillary tube 19, at its end closest to the cathode, and rotation is immediately started. Under the influence of the electrical field, separation occurs within the channel and the separated zones migrate towards the anode, according to well established principles of electrophoresis. If the components to be separated are cationic, then the polarity of the electrodes must be reversed, but this is unusual. As each zone migrates past the rotating seal, it is swept out of the tube by the perpendicular eluting jet, and can be collected in a series of test tubes, a fraction collector, or fed to optical sensors, particle counters, or other appropriate devices. If the sample is composed of particulate material, such as erythrocytes, leukocites, etc., the zones are clearly visible and sample collection can be adequately visually monitored. For colorless samples, such as soluble proteins, an ultraviolet monitor can be used at the effluent side, i.e., with tube 37, as is customary in the monitoring of liquid chromatography effluents. The optimum rate of eluent flow for a given separation must be determined experimentally, as it will depend on the electrical field applied and the mobility of the fractions. Using visible particles, such as erythrocytes or dyes, it is easy to establish minimum eluent flow which will prevent any particles from passing through the rotating seal fraction collector into the anode compartment. Typical operational data are: diameter of tube 13 in the range of 0.1 to 0.5 cm., electric field in the range of 5 to 30 volts/cm., the flow of the eluting buffer in the range of 0.01 to 0.2 ml./min.

A second typical example of an electrophoresis apparatus according to the present invention including a rotating seal fraction collector is illustrated in FIG. 3, and is designated generally at 38. The apparatus 38 includes a supporting base plate 39 on which is rotatably mounted the electrophoresis tube 40, the tube 40 being rotatably supported by a pair of spaced conventional bearing block assemblies 41, 41 including angularly spaced positioning rollers 42 engaging the tube. A friction pulley 43 driven by an electric motor, not shown, drivingly engages the intermediate portion of tube 40. The rotating cathode chamber 44 is rigidly secured axially to one end of tube 40, and its cathode electrode is energized from a negative voltage supply wire 45 via a suitable contact brush element 46.

The apparatus 38 differs from that in FIG. 1 in two important respects:

1) Instead of a capillary tube to inject the sample into the electrophoresis tube, a pivoted sliding gate sample injector is employed, shown at 46. As shown in FIG. 5, gate 46 is pivoted on a longitudinal pivot bolt 47 in the body of chamber 44 and is retained by a longitudinal stop bolt 48 in the chamber body extending through an arcuate slot 49 in gate 46, allowing the gate to be rotated outwardly from a normal position flush with chamber 44 to a filling position, shown in FIG. 5. The gate 46 has a central lumen 50 normally registering with the bore or lumen 51 of tube 40, and which is rotatable to the sealed displaced filling position of FIG. 5. Gate 46 has a passage 52 leading to a conventional rubber septum holder 53 provided on the periphery of the gate through which a sample may be injected into lumen 50 by means of a hypodermic needle 54, or the like.

Alternatively, a closable conduit fitting may be provided at 53, and the sample may be injected through a tube detachably connected to the conduit fitting. A bleed slot 56 is provided in gate 46 which registers with the electrophoresis tube lumen in the filling position of the gate, shown in FIG. 5, and allows bleeding of the cathode compartment and of the tube 40 through a bleed tube 57 which may be detachably connected at 58 to a port leading to slot 56, permitting air to be eliminated from the system. A finger lug 59 is provided on the periphery of gate 46 for manually rotating the gate around the pivot bolt 47. In the gate position of FIG. 5, lumen 50 is completely isolated from the lumen of tube 40, allowing it to receive the sample, and allowing the lumen of tube 40 and the cathode compartment to be bled, as above described. To start operation after filling, the sliding gate 46 has only to be pushed into its central flush registering position relative to cathode chamber 44, shown in FIG. 3.

2) The other important difference is that the rotating tube 40 is made of heavy-walled glass (0.5 to 1 cm. wall thickness). This eliminates the need for attachment of the separate fraction collector adaptor blocks 27, 28 of FIGS. 1 and 2. The stationary anode chamber, shown at 60, has a cylindrical inlet tube segment 61 which is ground flat at its end 62, and is perpendicular to the tube axis. Rotating tube 40 similarly has a flat perpendicular end surface 63 sealingly engaging surface 62. The stationary surface 62 has a diametrically oriented groove 64 traversing the lumen 65 of tube segment 61. An afferent elutant tube 66 is connected to a passage leading to one end of groove 64, and an efferent elutant tube 67 is connected to a passage leading to the other end of said groove 64, for the flow of the eluting buffer, providing operation similar to that described for the embodiment illustrated in FIGS. 1 and 2, but permitting a more precise arrangement of the two mating surfaces of the rotating seal fraction collector assembly, its stationary part still being provided with a groove and afferent and efferent tubing 66 and 67, for the flow of the eluting buffer.

Another embodiment according to the present invention of an electrophoresis apparatus incorporating a rotating seal fraction collector is shown in FIGS. 6 and 7, said apparatus being designated generally at 68. It is characterized by the fact that electrophoretic migration occurs within the lumen formed between an outer rotating glass cylinder 69 and an inner stationary tube 70. The cathode compartment, shown at 71, is fixedly secured to and rotates with the rotating tube 69, a suitable rotating seal 72 providing sealing against the stationary tube 70. Rotation of the cylinder 69 takes place within the bearings 73, 73 as a result of torque applied to a pulley 74 secured on tube 69. The ground flat and true annular end 75 of tube 69 provides sufficient mating surface for the rotating seal fraction collector at the area where it mates with the flat annular surface 76 of the stationary anode compartment 77. Said surface 76 has radial grooves 78 communicating with a circular groove 79 formed concentrically with said surface, said circular groove being connected by a passage 80 to an afferent elutant tube 81. The radial grooves 78 are aligned with radial conduits 82 extending through the wall of tube 70 and connected to the common efferent elutant tube 83. The sample injection tube 84 extends through a sealing plug 85 and has radial injection arms 86 which extend through the wall of tube 70 and are arranged to inject the sample fluid into the annular lumen 86' between the two cylinders 70, 69 at some distance (1-3 cm.) from the cathode end of the migration channel, and is spread in a circular annulus in the lumen due to the rotation of the fluid.

Elution of the fractions occurs at the rotating seal fraction collector (at surfaces 75, 76) by means of the eluting action at the radial channels 78, 82 traversing lumen 86' of the elutant traveling from inlet tube 81 to outlet tube 83, providing jets of eluting fluid perpendicular to the direction of electrophoretic migration at the rotating seal fraction collector. Any desired number of radially aligned elution channels 78, 82 may be provided, uniformly distributed around the annulus defined by the sealing surfaces 75, 76, and also, any desired number of radial sample injection arms 86 may be provided. The internal tube 70 may be cooled by circulating a suitable cold medium via inlet and outlet conduits 87 and 88. Cooling of the outer tube 69, as in the previously described embodiments, can be provided by circulating cold air around the apparatus or by placing it in a cold box, refrigerator, or the like.

FIG. 8 shows the apparatus 68 arranged vertically, with anti-convective material 89 in the lumen 86', supported on an annular screen 90, and an annular semipermeable membrane 91 provided in the electrophoresis lumen at the anode chamber side of the rotating seal fraction collector. Screen 90 may be secured to fixed tube 70.

Still another embodiment of the present invention is illustrated in FIGS. 9 and 10, wherein the apparatus is designated generally at 92, and wherein the electrophoretic migration again occurs within the lumen 94 formed between an outer rotating glass cylinder 93 and an inner rotating tube 95. This embodiment differs from that of FIGS. 6 and 7 in that both the inner tube 95 and the outer tube 93 can be rotated at will, either synchronously or at different speeds. Thus, the outer cylinder 93 carrying the cathode compartment 96 is supported on blocks 105, 105 by bearing assemblies 97, 97 and is provided with a driving pulley 98. The anode compartment 99 is stationary and is provided with a central bearing socket assembly 100 which rotatably receives the end pilot bearing member 101 secured in the right end of inner tube 95, as viewed in FIG. 9. At its opposite end, tube 95 is rotatably supported on a block 106 by a bearing assembly 102. An annular rotating seal 103 is provided between cathode compartment 96 and inner tube 95. Inner tube 95 is provided with a driving pulley 104.

A sample injection tube 107 communicatively connects lumen 94 with a closable injection element 108, such as a septum assembly with a rubber septum disc penetrable by a hypodermic needle or a closable conduit fitting to which a sample injection tube can be detachably connected. Coolant can be circulated through the inner tube 95 via a stationary axial coolant supply tube 109 extending sealingly and rotatably through a fitting 110 secured in the left end of tube 95, as viewed in FIG. 9, and provided with a coolant exit passage 111.

The rotating seal fraction collector assembly comprises mating annular outer sealing surfaces 112, 113 between outer tube 93 and stationary anode chamber 99, and mating annular sealing surfaces 114, 115 between inner tube 95 and said stationary anode chamber. Elution jet fluid is provided by an afferent tube 116 leading to a radial groove 117 in surface 113 which is aligned with a radial groove 118 in surface 115 communicating with an efferent tube 119. This arrangement provides a single elution jet across lumen 94. A triple elution jet arrangement is illustrated in FIG. 11, wherein three equally spaced sets of radially aligned grooves 117, 118 are provided in the surfaces 113, 115, the outer ends of the radial grooves 117 being connected by a circular groove 120 in surface 113 concentric therewith, and the inner ends of grooves 118 being connected by a circular groove 121 in surface 115 concentric therewith. Afferent elutant tube 116 is connected to outer circular groove 120 and efferent elutant tube 119 is connected to inner circular groove 121.

In the embodiment illustrated in FIGS. 12 and 13, the arrangement is generally similar to that of FIGS. 3 to 5, the apparatus is positioned vertically, and the electrophoresis column tube 140 is held stationary, whereas the anode compartment 160 is rotated. The elutant afferent tube 166 is connected to a circular groove 167 concentrically formed in the flat bottom rotational sealing surface 168 of the stationary vertical tube 140. The anode compartment 160 has a vertical top tube 169 with a flat top rotational sealing surface 170 mating with the sealing surface 168. Surface 168 has an inner concentric groove of circular shape, shown at 171, connected to the elutant efferent tube 192. A radial jet passage 172 in the wall of tube 169 has a vertical inlet portion 173 exposed to circular groove 167. Diametrically aligned with jet passage 172 is an opposite passage 174 in the wall of tube 169 communicating with inner circular groove 171 and with the efferent tube 192. Jet passages 172, 174 are relatively close to the plane of face 170. Vertical tube 140 contains anti-convective material 175 supported on a screen 176. A semi-permeable membrane 177 is mounted in the lumen of tube 169 below the elution jet path defined by the aligned passages 172, 174.

Experiments with injection of colored liquid into a stationary and otherwise sealed column of fluid, with an inlet and outlet for the eluting jet positioned diametrically across the tube, have shown close interaction of inflowing and outflowing fluid, if the inlet and outlet are closely spaced. This interaction results in a straight flow of the eluting jet, visualized as a well-defined colored jet connecting inlet and outlet. As the distance between inlet and outlet is increased, this interaction decreases, and broadening of the jet in the middle is visible. At sufficient distance of the inlet and outlet, all visible interaction ceases, and one has a classical situation of an injection into a relatively infinite reservoir, and corresponding outflow on the other side. Obviously, the maximum distance for good geometry maintenance of the eluting jet is governed by principles of fluid dynamics. In the rotating seal fraction collector of the present invention this is further complicated by the fact that the jet is rotating with respect to The above-described embodiments serve to illustrate but do not limit the applicability of the disclosed rotating seal fraction collector principle for the design of electrophoretic instruments. Obviously, on the same principle other configurations can be designed. Such additional configurations will be obvious to those versed in the art of electrophoresis. For example: (1) In the abovedescribed instruments, non-gasing electrodes were assumed, as it is essential that the total volume of the apparatus be constant, thereby forcing the inflowing jet of eluting buffer to flow out through the only opening available, i.e., the efferent line. If for reasons of buffer composition, or other reasons, gasing electrodes are to be employed, this can be easily accomplished by fitting either or both of the electrode compartments with a semi-permeable or an ion exchange membrane, supported in a rather rigid fashion so as not to cause pulsation, and placing the gasing electrodes external to said membrane and allowing free escape of the gas.

(2) Elution of the fractions causes their dilution. This is of little consequence for cells, as they can be easily reconcentrated by sedimentation or gentle centrifugation. Not so for proteins, where concentration is more difficult. Dilution can be minimized by preventing physically the migration of the proteins much beyond the rotating seal fraction collector interface. This is accomplished by interposing into the migration path a semi-permeable membrane, as shown in FIGS. 8 and 12. Such membranes permit the passage of electric current, but are of sufficiently small pores to retain proteins. This membrane will be located on the anodic side of the rotating seal fraction collector, preferably 0.1 to 0.3 cm. away from the rotating seal fraction collector interface.

(3) In sealed vessels, electro-osmosis, due to electrical charge of the wall of the electrophoretic vessel, causes a parabolic distortion of the fronts of the migrating zones, the parabola pointing in the direction of the anode. To minimize electro-osmosis, the glass vessels can be coated with a variety of substances, well-described in the electrophoretic literature. Should there still be some bowing of the profile, this can be corrected by causing liquid flow in the opposite direction, i.e., towards the cathode. Such counterflow can be also used to lower the migration rate of moving fractions, this having an effect similar to that of lengthening the electrophoretic apparatus. This counterflow, for either of the two effects, can be easily accomplished by means of the rotating seal fraction collector. It is sufficient to bleed slowly, at a constant rate, by means of gravity or an aspirating syringe pump, some of the fluid from the cathode compartment. This will be automatically replenished by part of the inflowing elution buffer, which will now have to serve two purposes: provide replacement fluid for the counterflow, and provide some excess fluid for the elution system.

(4) In some instances, notably in so-called isotachophoresis, discontinuous buffer systems are used, the sample being injected in between a leader buffer, and a terminator buffer. This can be easily accomplished in the above instruments, by filling the cathode compartment with one buffer, the tubes and anode with another. Rotation of the tube will minimize mixing of the two buffers. This is easiest to achieve in the design illustrated in FIG. 3, as the sliding gate used for sample injection prevents all cross-contamination.

Finally, the herein-disclosed rotating seal fraction collector can be utilized for fraction collection from channels stabilized by gels. The cast gel has to terminate sharply at or slightly before the rotating seal fraction collector interface. A similar concept can be also used with columns filled with granular support materials, retained by a screen at or near the rotating seal fraction collector interface, as in FIGS. 8 and 12. Rotational stabilization of the electrophoresis channel is necessary in free fluid electrophoresis but not in stabilized columns. Therefore, such instruments can be mounted vertically, for example, the electrophoretic column being stationary, the rotating element being the anode compartment, as in FIG. 12, or an interposed adaptor. The afferent and efferent tubes for the flow of eluting buffer can be mounted on either the stationary or the rotating part of the rotating seal fraction collector. A semipermeable membrane is located immediately below the rotating seal fraction collector, to cause retention of the emerging proteins.

In either case, elution of the fractions as they emerge from the packed part of the column is facilitated by the constantly changing direction of flow of the eluting buffer. This is a distinct advantage over the design of such elution systems in presently available electrophoretic columns. Typical of these is the Uniphor apparatus manufactured by the LKB Instrument Co., of Bromma, Sweden. It contains a small elution chamber, fitted between a screen holding the packed material or gel, and a semipermeable membrane, located closer to the anode. This membrane, while offering little resistance to current flow, retains all proteins in the fractions, and these are rinsed out by a flowing stream of buffer. As the column is of circular cross-section, whereas the jet of eluting buffer is uni-directional, stagnating pockets are easily formed, cross-contaminating the fractions previously electrophoretically separated. To avoid such cross-contamination, rapid flow of buffer may be used, resulting however, in excessive dilution of the sample. This is decreased by the use of the herein-disclosed rotating seal fraction collector, as the direction of flow of the eluting buffer is constantly changing.

While certain specific embodiments of improved electrophoretic fractional elution apparatus employing a rotational seal fraction collector have been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiments.

What is claimed is:

1. A fractional elution apparatus comprising an electrophoresis column having two longitudinally aligned abutting parts with registering lumens, means to rotate the parts axially relative to each other, and means defining a rotating seal fraction collector for the elution of fractions separated electrophoretically within the lumens, said collector comprising two mated flat surfaces perpendicular to the axis of the column at the abutting ends of said parts, one of said flat surfaces rotating and the other flat surface being stationary, and means for directing at least one narrow jet of eluting buffer perpendicular to the axis of rotation substantially at the interface formed by said mated surfaces.

2. The elution apparatus of claim 1, and wherein one of said abutting column parts comprises a horizontal tube of circular cross section rotating around its axis, a rotating electrode compartment attached to said tube, means to introduce a sample into said tube at its end closest to the rotating electrode compartment, and wherein the other abutting column part comprises a stationary electrode compartment, said mated flat surfaces being at the interface between said rotating tube and said stationary electrode.

3. The elution apparatus of claim 1, and wherein said electrophoresis column is vertically positioned and wherein one column part is stationary and contains anti-convective material, said one part being provided with a stationary electrode compartment at one end, and wherein the other column part comprises a rotatable electrode compartment, said mated flat surfaces being at the interface between said stationary column part and said rotatable electrode compartment associated with said rotating seal fraction collector.

4. The elution apparatus of claim 1, and wherein said electrophoresis column comprises two concentric cylinders and wherein said registering lumens comprise the space between the cylinders, and wherein said means for directing the jet of eluting buffer is arranged to cause the jet to radially traverse the fluid contained within said lumens substantially at the interface defined by said mated surfaces.

5. The elution apparatus of claim 4, and wherein said concentric cylinders are horizontally mounted and are provided with means to independently rotate the cylinders around their axes, and wherein a rotating electrode compartment is provided, attached to an end of one of the cylinders, and means to introduce a sample into the lumen inside said one cylinder in close proximity to said rotating electrode compartment, and wherein a stationary electrode compartment is provided adjacent to the other end of said one cylinder, said mated flat surfaces being at the interface between said concentric cylinders and said stationary electrode compartment.

6. The elution apparatus of claim 4, and wherein said concentric cylinders are vertically mounted, and lumen between the cylinders containing anti-convective material, and wherein a first electrode compartment is provided at one end of the cylinders, and wherein a second electrode compartment is provided adjacent the other end of the cylinders, said mated flat surfaces being at the interface between the concentric cylinders and one of the electrode compartments.

7. The elution apparatus of claim 1, and wherein said electrophoresis column is provided with a semi-permeable membrane in the path of electrophoretic migration and located on the anodic side of the interface formed by said mated surfaces.

8. The elution apparatus of claim 7, and wherein said semi-permeable membrane is located between 0.1 and 0.3 cm. away from said interface.

9. The elution apparatus of claim 1, and wherein said electrophoresis column has a stationary part and a rotating part located on opposite sides of said interface, respective electrode compartments attached to the ends of said stationary and rotating column parts, and means to introduce a sample into the column at a location spaced a substantial distance along the column from said interface.

10. The elution apparatus of claim 9, and wherein said electrophoresis column is horizontally positioned and wherein said sample-introducing means is located adjacent to one of the electrode compartments.

11. The elution apparatus of claim 1, and wherein said electrophoresis column is vertically positioned and has a stationary part and a rotating part at opposite sides of said interface, said column parts being provided at their ends with respective electrode compartments, one being cathodic and the other anodic.

12. The elution apparatus of claim 11, and wherein one column part contains anti-convective material and the other column part is provided with a semi-permeable membrane and is attached to the anodic electrode compartment.

* * * * *

UNITED STATES PATENT AND TRADEMARK OFFICE
CERTIFICATE OF CORRECTION

PATENT NO. : 4,040,940
DATED : August 9, 1977
INVENTOR(S) : Milan BIER

It is certified that error appears in the above-identified patent and that said Letters Patent are hereby corrected as shown below:

Change the Assignee to read:

-- The Government of the United States, as represented by the Administrator of Veterans' Affairs.--

Signed and Sealed this

Twenty-eighth Day of February 1978

[SEAL]

Attest:

RUTH C. MASON
Attesting Officer

LUTRELLE F. PARKER
Acting Commissioner of Patents and Trademarks